United States Patent [19]

Jones et al.

[11] Patent Number: 4,570,000
[45] Date of Patent: Feb. 11, 1986

[54] NITROGEN HETEROCYCLES

[75] Inventors: Derrick F. Jones, Macclesfield; Keith Oldham, Cheadle, both of United Kingdom

[73] Assignee: Imperial Chemical Industries, PLC, London, England

[21] Appl. No.: 630,716

[22] Filed: Jul. 13, 1984

Related U.S. Application Data

[62] Division of Ser. No. 356,503, Mar. 9, 1982, Pat. No. 4,460,584.

[30] Foreign Application Priority Data

Mar. 13, 1981 [GB] United Kingdom ............... 8108048

[51] Int. Cl.$^4$ ................. C07D 401/2; C07D 403/12; A61K 31/505; A61K 31/44
[52] U.S. Cl. ................................ 514/237; 548/184; 548/193; 548/230; 548/128; 544/194; 514/252; 514/326; 514/364; 514/363; 514/397
[58] Field of Search ............ 548/184, 193, 230, 128; 424/249; 544/194

[56] References Cited

U.S. PATENT DOCUMENTS 4,460,584 7/1984 Jones et al. ................. 548/128

Primary Examiner—John Kight
Assistant Examiner—M. L. Moore
Attorney, Agent, or Firm—Cushman, Darby & Cushman

[57] ABSTRACT

The invention relates to nitrogen heterocycles which are histamine H-2 antagonists and which inhibit gastric acid secretion. According to the invention there is provided a guanidine derivative of the formula I:-

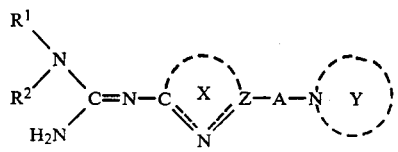

in which $R^1$ and $R^2$, same or different, are hydrogen or 1-10C alkyl, 3-8C cycloalkyl or 4-14C cycloalkylalkyl, each alkyl, cycloalkyl or cycloalkylalkyl optionally carrying one or more F, Cl or Br atoms, provided that one of $R^1$ and $R^2$ is halogen substituted, or $R^2$ is hydrogen and $R^1$ is $R^3$—E—W is which W is 2-6C alkylene optionally substituted by 1 or 2 1-4C alkyls, E is O, S, SO, $SO_2$ or $NR^4$ in which $R^4$ is H or 1-6C alkyl, $R^3$ is H or 1-6C alkyl optionally substituted by 1 or 2 1-4C alkyls, or $R^3$ and $R^4$ are joined to form a pyrrolidine, piperidine, morpholine, piperazine or N-methylpiperazine ring, or $R^2$ is H and $R^1$ is H, 1-10C alkyl, 3-8C cycloalkyl, 4-14C cycloalkylalkyl, 3-6C alkenyl, 3-6C alkynyl, 1-6C alkanoyl, 6-10C aryl, 7-11C aralkyl or 7-11C aroyl; ring X is a heterocyclic ring as defined in the specification; A is phenylene or 5-7C cycloalkylene, or a 1-8C alkylene into which is optionally inserted one or two groups; ring Y is a heterocyclic ring described in the specification: and the pharmaceutically-acceptable acid-addition salts thereof. Manufacturing processes and pharmaceutical compositions are also described.

6 Claims, No Drawings

NITROGEN HETEROCYCLES

This is a division, of application Ser. No. 356,503, filed Mar. 9, 1982, now U.S. Pat. No. 4,460,584, issued July 17, 1984.

This invention relates to nitrogen heterocycles which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, *Brit.J.Pharmac.* 1966, 27, 427) and the action of histamine at this receptor is blocked (antagonised) by classical "antihistamine" drugs such as mepyramine. The second histamine receptor has been named the H-2 receptor (Black et al., *Nature,* 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In UK Patent Application No. 2001624 and European Patent Publications Nos 6286, 6679, 30092 and 45155 there are described histamine H-2 receptor antagonists which are guanidino heterocycles carrying a side chain to the end of which is attached a modified guanidine residue. It has now been discovered that if this modified guanidine is replaced by a nitrogen heterocycle linked via the nitrogen atom there are obtained potent histamine H-2 receptor antagonists.

According to the invention there is provided a guanidine derivative of the formula I:

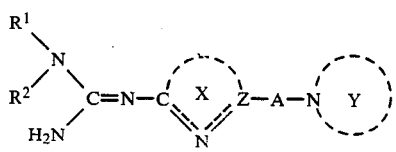

in which $R^1$ and $R^2$, which may be the same or different, are hydrogen atoms or branched or unbranched 1–10C alkyl, 3–8C cycloalkyl or 4–14C cycloalkylalkyl radicals, each alkyl, cycloalkyl or cycloalkylalkyl radical being optionally substituted by one or more halogen atoms selected from fluorine, chlorine and bromine atoms, provided that at least one of $R^1$ and $R^2$ is a halogen-substituted alkyl, cycloalkyl or cycloalkylalkyl radical, and provided that there is no halogen substituent on the carbon atom of the alkyl, cycloalkyl or cycloalkylalkyl radical which is directly attached to the nitrogen atom, or $R^2$ is a hydrogen atom and $—R^1$ is a radical of the formula II:

$$R^3—E—W— \qquad II$$

in which W is an unbranched 2–6C alkylene chain which is optionally substituted by one or two 1–4C alkyl radicals, E is an oxygen or sulphur atom, a sulphinyl or sulphonyl radical, or a radical of the formula $NR^4$ in which $R^4$ is a hydrogen atom or a 1–6C alkyl radical, $R^3$ is a hydrogen atom or an unbranched 1–6C alkyl radical which is optionally substituted by one or two 1–4C alkyl radicals, or $R^3$ and $R^4$ are joined to form, together with the nitrogen atom to which they are attached, a pyrrolidine, piperidine, morpholine, piperazine or N-methylpiperazine ring, or $R^2$ is a hydrogen atom and $R^1$ is a hydrogen atom or a 1–10C alkyl, 3–8C cycloalkyl, 4–14C cycloalkylalkyl, 3–6C alkenyl, 3–6C alkynyl, 1–6C alkanoyl, 6–10C aryl, 7–11C arylalkyl or 7–11C aroyl radical, the aryl, arylalkyl and aroyl radicals being optionally substituted on the aryl ring by one or two substituents selected from fluorine, chlorine and bromine atoms and 1–6C alkyl, 1–6C alkoxy, 1–6C alkylthio, trifluoromethyl, hydroxy and amino radicals; in ring X the dotted line is a double bond on one side of the nitrogen atom and Z is a carbon or nitrogen atom such that ring X is a 5- or 6-membered aromatic heterocyclic ring which contains at least one nitrogen atom and may optionally contain one or two additional hetero atoms selected from oxygen, nitrogen and sulphur atoms, which heterocyclic ring may, where possible, carry one or two optional substituents, the optional substituents on ring X being selected from fluorine, chlorine and bromine atoms and 1–6C alkyl, 1–6C alkoxy, 1–6C alkylthio, trifluoromethyl, hydroxy and amino radicals; A is a 1–8C alkylene chain which is optionally substituted by one or two 1–3C alkyl radicals and into which is optionally inserted, as part of the backbone of the chain, an NH or a 1–6C N-alkyl radical or one or two groups selected from oxygen and sulphur atoms and cis and trans vinylene, ethynylene, phenylene and 5–7C alkylene radicals, provided that no two insertions selected from oxygen and sulphur atoms and NH and N-alkyl radicals are directly attached one to the other, and provided that when an optional insertion is made in chain A which results in the inserted group being directly attached to ring Y the inserted group is other than an oxygen or sulphur atom or an NH or N-alkyl radical, or A is a 5–7C cycloalkylene radical or phenylene radical; ring system Y is a heterocyclic ring system which is a 5- or 6-membered heterocyclic ring which may be saturated, partially unsaturated or fully unsaturated and which optionally contains one to three additional hetero atoms or groups selected from oxygen, nitrogen and sulphur atoms and sulphinyl and sulphonyl radicals and which optionally contains a fused benzene ring, ring system Y being optionally substituted on a nitrogen atom by a 1–6C alkyl radical and on a carbon atom of the heterocyclic ring, where possible, by one, two or three groups selected from halogen atoms and 1–6C alkyl, 1–6C alkoxy, 1–6C alkanoyl, cyano, nitro, 2–6C alkoxycarbonyl, carbamoyl, 2–6C alkylcarbamoyl, 3–8C dialkylcarbamoyl, 1–6C alkanesulphonyl, hydroxy, amino, 1–6C alkylamino, 2–8C dialkylamino and methylsulphonylimino radicals and the optional benzene ring being optionally substituted by one or two substituents selected from halogen atoms and 1–6C alkyl, 1–6C alkoxy, 1–6C alkylthio, hydroxy and amino radicals; and the pharmaceutically-acceptable acid-addition salts thereof.

It is to be understood that, in the above formula I and throughout this specification, although the double bond in the guanidine radical has been inserted in a particular position, other tautomeric forms are possible, and this invention includes such tautomeric forms within its scope, both in terms of the compounds of the invention and in terms of the manufacturing processes. Similarly, when ring system Y is substituted by a hydroxy radical, that radical may exist in the tautomeric keto form. It is also to be understood that when A is or contains a cycloalkylene radical the groups attached to this radical may be in the cis or trans configuration. When A is or contains a cycloalkylene radical and/or when A is an alkylene chain substituted by one or two alkyl radicals, the compound of the formula I will, in most instances, contain at least one asymmetric centre. In such cases the compound of the formula I will therefore exist in at least two enantiomeric forms, the precise number being determined by the number of asymmetric centres. The biological activity, as hereinafter defined, of these enantiomeric forms may differ, and it is therefore to be understood that this invention encompasses the racemate of the formula I, including any possible diastereoisomeric forms, and any enantiomeric form which possesses the disclosed biological activity, it being a matter of common general knowledge to one skilled in the art how to separate diastereoisomeric forms and how to separate a racemate into its enantiomers and determine the biological activity of each.

A particular value for $R^1$ or $R^2$ when it is a halogen-substituted alkyl radical is a 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl or 2,2,3,3,4,4,4-heptafluorobutyl radical.

A particular value for $R^1$ or $R^2$ when it is a halogen-substituted cycloalkyl radical is a 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl or 2-chloro-2,3,3,4,4-pentafluorocyclobutyl radical.

A particular value for $R^1$ or $R^2$ when it is a halogen-substituted cycloalkylalkyl radical is a (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl or (2-chloro-1,2,3,3,4,4-hexafluorocyclobutyl)methyl radical.

A particular value for $R^1$ and $R^2$ when it is an alkyl radical is a methyl, ethyl, propyl, isopropyl or butyl radical.

A particular value for $R^1$ or $R^2$ when it is a cycloalkyl radical is a cyclopropyl or cyclobutyl radical.

A particular value for $R^1$ or $R^2$ when it is a cycloalkylalkyl radical is a cyclopropylmethyl or cyclobutylmethyl radical.

A particular value for the optional substituent on W is a methyl radical.

A particular value for $R^3$ is a hydrogen atom or a methyl radical.

A particular value for $R^4$ is a hydrogen atom or a methyl radical.

A particular value for the radical of the formula II is a 2-methoxyethyl, 2-hydroxyethyl, 2-methylthioethyl or 2-dimethylaminoethyl radical.

When $R^2$ is a hydrogen atom a particular value for $R^1$ is a hydrogen atom or a methyl, ethyl, propyl, isopropyl, butyl, cyclohexyl, cyclohexylmethyl, allyl, propargyl, acetyl, phenyl, benzyl or benzoyl radical, the phenyl, benzyl and benzoyl radicals being optionally substituted on the phenyl ring by one or two substituents selected from fluorine, chlorine and bromine atoms and methyl, methoxy, methylthio, trifluoromethyl, hydroxy and amino radicals.

A particular value for ring X is an oxazole, thiazole, imidazole 1,2,4-thiadiazole, 1,2,4-oxadiazole, 1,2,3-triazole, 1,2,4-triazole, pyrazole, pyrazine, pyridine, pyrimidine or 1,3,5-triazine ring.

A particular value for the optional substituent on ring X when it is an alkyl, alkoxy or alkylthio radical is a methyl, methoxy or methylthio radical.

A particular value for —A— is a phenylene, cyclopentylene, cyclohexylene, trimethylene, tetramethylene, pentamethylene, thioethylene, thiotrimethylene, thiotetramethylene, thiopentamethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, oxyethyleneoxymethylene, iminoethylene, iminopropylene, vinylenepropylene, oxymethylenevinylene, 1,3-phenylene, 1,3-cyclopentylene, methylene-1,4-phenylene, ethyleneoxymethylene-1,4-phenylene, oxy-1,3-phenylenemethylene or thiomethylene-ethynylenemethylene radical. These values for —A— are written reading from left to right in formula I such that the first named part of the radical is attached to ring X and the last named part of the radical is attached to ring Y. Thus, for example, when —A— is a thiotrimethylene radical, the compound of the formula I contains the part structure III:

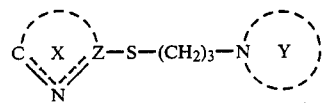

III

A particular value for the optional nitrogen substituent on ring system Y is a methyl radical.

A particular value for the optional substituent on the carbon atom of the heterocyclic ring in ring system Y is one, two or three groups selected from fluorine, chlorine and bromine atoms and methyl, methoxy, formyl, cyano, nitro, methoxycarbonyl, carbamoyl, methylcarbamoyl, dimethylcarbamoyl, methanesulphonyl, hydroxy, amino, methylamino, dimethylamino and methylsulphonylimino radicals.

A particular value for the optional substituent on the optional benzene ring is one or two substituents selected from fluorine chlorine and bromine atoms and methyl, methoxy, methylthio, hydroxy and amino radicals.

A particular value for ring system Y is one of the formula IV, V, VI, VII, VIII, IX, X, XI or XII:

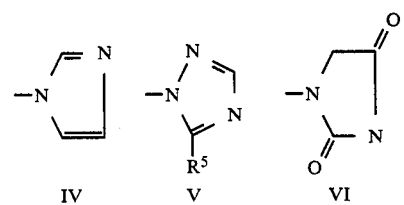

IV  V  VI

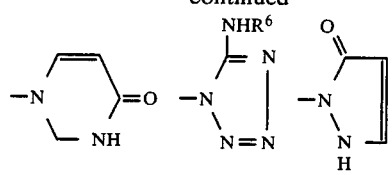
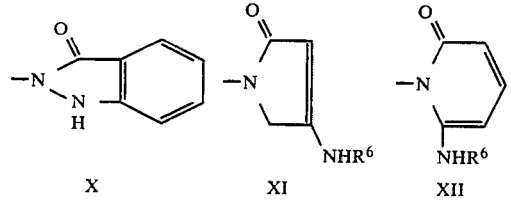

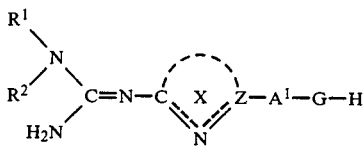

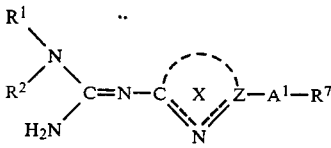

with a compound of the formula XV or XVI respectively:

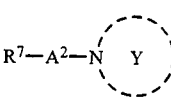

XV

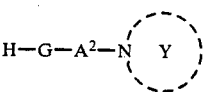

XVI in which R⁵ is a hydrogen atom or a radical of the formula NHR⁶ and R⁶ is a hydrogen atom or a 1-6C alkyl (for example methyl) radical. A further particular value for ring system Y is a 2-hydroxyimidazol-1-yl, 2,4-dihydroxyimidazol-3-yl, 2-methylimidazol-1-yl, 2-formylpyrrol-1-yl, 2-methylsulphonylimino-3-methyl-4-imidazolin-1-yl, 3-methyl-1,2,4-triazol-1-yl, 3-amino-1,2,4-triazol-1-yl, 5-amino-1,2,3,4-tetrazol-2-yl, 2-oxo-1,2-dihydropyrid-1-yl, 2,3-dioxo-4-methylpiperazin-1-yl or piperidin-1-yl radical.

The following are six preferred features of the guanidine derivative of the formula I. When any one of these features is taken, either singly or in combination, with the other general or particular features of the guanidine derivative listed above, there are obtained preferred sub-groups of compounds within the above general definition.

1. $R^2$ is a hydrogen atom and $R^1$ is a 2,2,2-trifluoroethyl radical.
2. Ring X carries no optional substituent.
3. Ring X is a pyrimidine ring in which A is linked at the 2-position.
4. A is a pentamethylene, oxyethylene, oxytrimethylene, oxy-1-methylethylene, thiotrimethylene or oxy-1,3-phenylenemethylene radical.
5. Ring system Y is of the formula IV, V, VI, VII, VIII, IX, X, XI or XII given above in which $R^6$ is a hydrogen atom or a methyl radical.
6. Ring system Y is of the formula IV given above.

Particular compounds of the invention are set out in the Examples. A preferred compound is 1-[3-(4-[2-(2,2,2-trifluoroethyl)guanidino]pyrimid-2-yloxy)-propyl]imidazole (Example 6).

A suitable pharmaceutically-acceptable acid-addition salt of the guanidine derivative of the formula I is, for example, a salt formed with hydrochloric, hydrobromic, phosphoric, sulphuric, acetic, citric or maleic acid.

The guanidine derivative of the invention may be manufactured by methods in which the actual chemical reactions involved are known in themselves. The following processes, $R^1$, $R^2$, A, ring X and ring system Y having the meanings stated above, unless indicated otherwise, are therefore provided as further features of the invention.

The process of the invention is characterised by:
(a) for those compounds in which the group inserted into A is an oxygen or sulphur atom, reaction of a compound of the formula XIII or XIV:

in which G is an oxygen or sulphur atom or an NH or N-alkyl radical, $R^7$ is a displaceable radical and $A^1$ and $A^2$ are fragments of A, including direct bonds, and are such that $A^1$—G—$A^2$ falls within the definition of A given above. $R^7$ is, for example, a halogen atom, for example a chlorine or bromine atom. When $R^7$ is directly attached to ring X, $R^7$ may, for example, be a methylsulphinyl or methylsulphonyl radical.

(b) formation of ring system Y by cyclisation of an open chain precursor thereof. Thus when ring system Y is 2-hydroxyimidazol-1-yl, the precursor may contain the partial formula XVII:

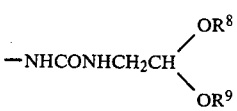

XVII in which $R^8$ and $R^9$ are 1-6C alkyl, for example ethyl, radicals or $R^8$ and $R^9$ are joined to form an ethylene or propylene radical. The cyclisation may be carried out using an aqueous mineral acid such as hydrochloric acid. When ring system Y is 2,4-dihydroxyimidazol-3-yl, the precursor may contain the partial formula XVIII or XIX:

 XVIII

 XIX in which $R^{10}$ is a hydrogen atom or a 1-6C alkyl (for example methyl or ethyl), phenyl or benzyl radical. The cyclisation may be carried out using a base such as sodium methoxide in methanol or potassium hydroxide in ethanol. When ring system Y is 2-methylsulphonylimino-3-methyl-4-imidazolin-1-yl, the precursor may contain the partial formula XX:

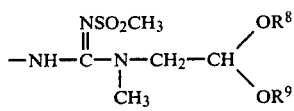 XX

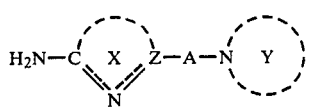 XXVI in which $R^8$ and $R^9$ are as described above. The cyclisation may be carried out using an aqueous mineral acid such as hydrochloric acid. When ring system Y is of the formula VI, the precursor may contain the partial formula XXI:

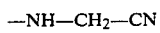 XXI

The cyclisation may be carried out by reaction with potassium cyanate in aqueous acetic acid followed by treatment with concentrated aqueous hydrochloric acid.

(c) reaction of a compound of the formula XIII:

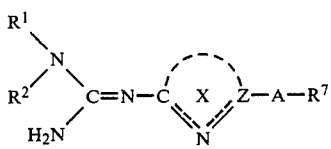 XXII in which $R^7$ is a displaceable radical with a compound of the formula XXIII:

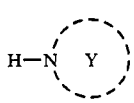 XXIII $R^7$ may, for example be a halogen atom, for example a chlorine, bromine or iodine atom.

(d) for those compounds in which Z is a nitrogen atom, reaction of a compound of the formula XXIV:

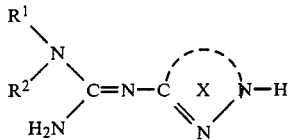 XXIV with a compound of the formula XXV:

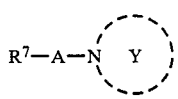 XXV in which $R^7$ is a displaceable radical. $R^7$ is, for example, a halogen atom, for example a chlorine, bromine or iodine atom.

(e) construction of the guanidine radical attached to ring X by reaction of the appropriate thiourea, or a 1-6C S-alkyl (e.g. S-methyl) or S-benzyl derivative thereof, or a salt of such a derivative, with the appropriate amine. The guanidine radical in the compound of the formula I contains three nitrogen atoms each of which carries different substituents. The appropriate amine for use in this reaction may therefore be ammonia, an amine of the formula $R^1R^2NH$ or an amine of the formula XXVI:

The reaction may be conducted using an excess of one of the reactants as a diluent or solvent, or an additional diluent or solvent, for example methanol or ethanol, may be added. In many cases it is advantageous to use a catalyst such as mercuric oxide, lead oxide or sodium hypochlorite. The reaction may be conducted at ambient temperature or it may be accelerated or completed by the application of heat, for example by heating to the boiling point of the diluent or solvent.

(f) construction of the guanidine radical attached to ring X by reaction of the appropriate cyanamide with the appropriate amine. Since the guanidine radical in the compound of the formula I contains only one unsubstituted nitrogen atom there are two appropriate amines, namely the amine of the formula $R^1R^2NH$ or of the formula XXVI given above.

(g) for those compounds in which ring X is a thiazole ring, reaction of a compound of the formula XXVII:

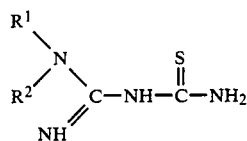 XXVII with a compound of the formula XXVIII:

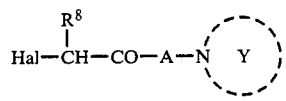 XXVIII in which Hal is a chlorine or bromine atom and $R^8$ is a hydrogen atom or the optional substituent on the thiazole ring. The reaction may be conducted in a diluent or solvent such as acetone and may be accelerated or completed by the application of heat, for example by heating to the boiling point of the diluent or solvent.

When the process of the invention manufactures the compound of the formula I in the form of the free base and an acid-addition salt is required, the compound of the formula I in the free base form is reacted with an acid which affords a pharmaceutically-acceptable anion.

The starting materials of the formula XIII and XIV for use in process (a) may be prepared by separate construction of the two side chains on the appropriate ring X. Thus the left hand side chain may be constructed by reduction of a nitro group to an amino group, reaction of this amino group with an isothiocyanate of the formula $R^1R^2N=C=S$, and finally reaction of the resulting thiourea with ammonia in the presence of mercuric oxide. The method of construction of the right hand side chain may vary depending on the nature of ring X, the nature of the atom in ring X to which $A^1$ is attached (carbon or nitrogen) and the presence or absence of inserted atoms or groups in chain $A^1$. When $A^1$ contains no inserted group, or the inserted group is a phenylene radical and Z is a carbon atom, it is preferable to construct ring X with the right hand side chain already in place. Thus, for example, when ring X is a pyrimidine ring, it may be formed by reaction of a suitably substituted amidine with 2-chloroacrylonitrile to give the corresponding 4-aminopyrimidine derivative. When the inserted group in A¹ is a cycloalkylene radical, the chain A¹ may be constructed by a conjugate addition to the corresponding cycloalk-2-enone. When the inserted group in A¹ is a vinylene or ethynylene radical, A¹ may be introduced by formation of the double or triple bond by standard coupling methods. When the inserted group in A¹ is an oxygen or sulphur atom or an NH or N-alkyl radical, the right hand side chain may be built up by a method similar to that in process (a) itself. When Z is a nitrogen atom, the right hand chain may be formed by a method similar to that in process (d).

The starting materials of the formulae XV and XVI for use in process (a) may be prepared by a method similar to that described in process (c), that is by reaction of a compound of the formula XXIII with a suitably-substituted carbon chain, for example as illustrated in Examples 2 to 14.

The starting material for use in process (b), the open chain precursor, may be prepared by reaction of a compound of the formula XXIX:

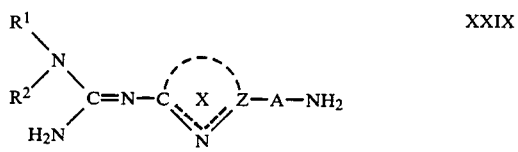

with a suitable reagent. Thus, for example, when the precursor contains the partial formula XVII, a suitable reagent is one of the formula XXX:

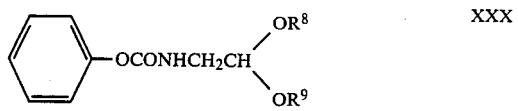

for example as illustrated in Example 15. When the precursor contains the partial formula XVIII or XIX, a suitable reagent is one of the formula XXXI or XXXII respectively:

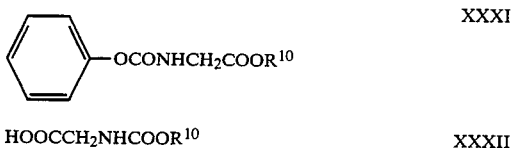

for example as illustrated in Examples 16 and 18 respectively. When the precursor contains the partial formula XX, a suitable reagent is dimethyl(methylsulphonylimino)dithiocarbonate followed by reaction of the product with a compound of the formula XXXIII:

for example as illustrated in Example 17. When the precursor contains the partial formula XXI, a suitable reagent is chloroacetonitrile, for example as illustrated in Example 19. The intermediate of the formula XXIX may itself be prepared by the methods described in Belgian Pat. No. 866155, UK Patent Application No. 2001624 and European Patent Publications Nos. 6286, 6679, 30092 and 45155.

As noted above, the quanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastrointestinal bleeding due to trauma.

The histamine H-2 antagonist activity may be demonstrated on standard tests, for example by the ability of the compound of the formula I to inhibit the histamine-induced uptake of aminopyrine into the acid space of parietal cells.

The aminopyrine test is carried out as follows:

Gastric mucosa from the New Zealand white rabbit is removed from the underlying muscel and washed in Buffer 1 [containing per liter NaCl; (8.007 g.), KCl (0.201 g.), $Na_2HPO_4$ (0.113 g.), $KH_2PO_4$ (0.204 g.), $CaCl_2.2H_2O$ (0.132 g.), $MgCl_2$ (0.101 g.) and glucose (1 g.), adjusted to pH 7.4 with NaOH]. The tissue is finely chopped, suspended in Buffer 1 and washed three times with Buffer 1. The tissue is then suspended in dispersion medium [collagenase (Sigma Chemical Co., Type V; 100 mg.) and bovine serium albumin (Miles Laboratories Ltd., Fraction V; 100 mg.) in Buffer 1 (100 ml.); 50 ml. per 10 g. net weight of tissue] and incubated at 30° C. and pH 7.4 (maintained by continuous monitoring) with stirring under an oxygen atmosphere. After 30 minutes the tissue is allowed to settle and the supernatant liquid is removed. Fresh dispersion medium (50 ml. per 10 g. wet weight of tissue) is added and incubation is continued with the tissue being largely dispersed into glands and whole cells after 40-60 minutes. Any remaining large pieces of tissue are removed by filtration through nylon mesh. The mixture of glands and cells is collected by centrifugation at 200×g. and suspended in Buffer 1 containing 1% bovine serum albumin (Miles Laboratories Ltd., Fraction V). Finally the cells and glands are washed 3 times with Buffer 1 and suspended in Buffer 2 [containing Eagles MEM (500 ml.), Aprotinin (Sigma Chemical Co., 10 mg.) and HEPES (2-[4-(2-hydroxyethyl)piperazin-1-yl]ethanesulphonic acid; 150 mM., 20 ml.) adjusted to pH 7.4 with NaOH; 150 ml. per 10 g. wet weight of tissue]. The tissue suspension is stirred under an oxygen atmosphere at 32° C. for at least 1 hour before use. The tissue suspension is incubated with the test compound and aminopyrine (10 μM) labelled with $C^{14}$ on the dimethylamino group (0.1 μCi/ml.) for 20 minutes. The uptake of the aminopyrine is then stimulated by addition of histamine and the phosphodiesterase inhibitor ICI 63197 (Biochem.Soc.Special Publication 1, 1973, pp 127-132) to final concentrations of $10^{-5}M$. and $5 \times 10^{-7}M$. respectively. After 18 minutes the cells/glands are separated from the incubation medium by filtration of the suspension through glass microfibre filters. The cells/glands are quickly (<10 seconds) washed three times with ice-cold Buffer 1. The $C^{14}$ aminopyridine retained by the tissue is measured on a scintillation counter and the degree of inhibition of uptake by the test compound is calculated by reference to a control sample. The concentration of test compound giving 50% inhibition is then calculated graphically from a series of tests run at different concentrations.

All the compounds exemplified in this specification were tested on the aminopyrine test. All gave a 50% inhibition of uptake of aminopyrine at or below a concentration of 3 μM.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats or dogs provided with denervated fundic pouches, and whose gastric secretion is stimulated by administration of a secretagogue, for example histamine, pentagastrin, bethanechol or food.

The test in rats is carried out as follows:

Female rats (200–230 g.) are anaesthetized by intramuscular administration of urethane (1.5 g./kg.) and the trachea cannulated. A soft tube is passed down the oesophagus into the stomach and secured by a tie in the neck region. A multi-orifice plastic tube (3 mm. diameter) is passed into the antral region of the stomach, via an incision in the duodenum, and tied in place by means of a ligature around the pylorus. Saline (9 g./l. NaCl) is perfused through the stomach via the oesophageal cannula at a rate of 7 ml./minute and collected into beakers from the pyloric outlet over periods of 10 minutes. Acid secretion is stimulated by subcutaneous administration of the specific H-2 agonist dimaprit in a loading dose of 10 mg./kg. followed by an infusion of 30 mg./kg./hour. Acid output is computed by titration of the 10 minutes samples to an end point of pH 6.4 with 20 mM. NaOH. When secretion has reached a plateau (three consecutive readings within 5%) the test compound is administered intravenously via a cannula placed in the left external jugular vein. Secretion is then measured for a further 2 hours. A stock solution of each test compound is prepared (10 mg./ml. in DMSO) and appropriate dilution made with saline to enable injection in a dose volume of 1 ml./kg. (DMSO<2%).

The test in dogs provided with denervated fundic pouches is carried out as follows:

Male beagle dogs (14–22 kg.) are prepared with vagally denervated pouches of the fundic gland area by the method of Rudick et al. (*J.Surg.Res.* 1967, 7, 383). The animals are allowed 4–6 weeks to recover from surgery and a further period of 2–3 months prior to routine use, to allow for table training and standardization of secretory responses. The dogs are starved for 23 hours before use (water ad lib) and during experiments they are lightly restrained in cloth slings. After rinsing the pouch with warm water, histamine is infused subcutaneously at a rate of 10 μg./minutes. This dose of agonist produces a submaximal (60–90% of maximum) increase in acid output in all dogs used. Pouch secretions are collected over 15 minute periods into graduated glass test-tubes and the volume measured to the nearest 0.1 ml. A 500 μl. sample is diluted with 5 ml. of saline and titrated to pH 7.0 with 100 mM. NaOH. Total acid output is computed from the product of acid concentration and volume of juice secreted. Compounds are administered intravenously (0.1 ml./kg.) via a cephalic vein or orally in a gelatin capsule when a secretory plateau (3 consecutive readings within 10%) has been attained. Secretion is measured for a period of 3 hours following administration of test compound.

The results obtained in the aminopyrine test are predictive of activity in the rat and dog tests.

No overt toxicity or side effects were noted during the rat or dog tests. The compound 1-[3-(4-[2-(2,2,2-trifluoroethyl)guanidino]pyrimid-2-yloxy)propyl]imidazole was administered intravenously to groups of two anaesthetised rats and four conscious mice at doses which were respectively ten times and one hundred times the dose, in mg./kg., which produced an approximate 50% inhibition of gastric secretion in the anaesthetised rat. No toxic symptoms were noted in any of the dosed animals.

A number of compounds exemplified in this specification exhibit inhibition of acid secretion which shows little or no decline from peak inhibition for several hours.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspension, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or parenteral administration may also contain, or be co-administered with, one or more known drugs selected from antacids, for example aluminium hydroxide-magnesium hydroxide mixtures; antipepsin compounds, for example pepstatin; other histamine H-2 antagonists, for example cimetidine or ranitidine; ulcer healing agents, for example carbenoxolone or bismuth salts; anti-inflammatory agents, for example ibuprofen, indomethacin, naproxen or aspirin; prostaglandins, for example 16,16-dimethylprostaglandin $E_2$; classical antihistamines (histamine H-1 antagonists), for example mepyramine or diphenhydramine; anticholinergic agents for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical antihistamines (histamine H-1 antagonists), for example mepyramine or diphenhydramine and/or one or more steroidal anti-inflammatory agents, for example fluocinolone or triamcinolone.

A topical formulation may contain 1–10% w/w of the guanidine derivative of the invention. A preferred pharmaceutical composition of the invention is one suitable for oral administration in unit dosage form, for example a tablet or capsule which contains between 5 mg. and 500 mg. of the guanidine derivative, or one suitable for intravenous, subcutaneous or intramuscular injection, for example a sterile injectable containing between 0.1% and 10% w/w of the guanidine derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency and duration of action of the guanidine derivative of the present invention relative to cimetidine. Thus each patient will receive an oral dose of between 15 mg. and 1500 mg., and preferably between 20 mg. and 200 mg. of guanidine derivative or an intravenous, subcutaneous or intramuscular dose of between 1.5 mg. and 150 mg., and preferably between 5 mg. and 20 mg. of the guanidine derivative, the composition being administered 1 to 4 times per day. The rectal dose will be approximately the same as the oral dose. The composition may be administered less frequently when it contains an amount of guanidine derivative which is a multiple of the amount which is effective when given 1-4 times per day.

The invention is illustrated, but not limited, by the following Examples. The n.m.r. spectra are quoted in δ relative to tetramethylsilane (δ=0) as internal standard (s=singlet, d=doublet, t=triplet, q=quartet, m=multiplet, br=broad). The temperatures are in degrees Centigrade. The following contractions are used:

HOAc=acetic acid
DMF=dimethyl formamide
ether=diethyl ether
DMSO=dimethylsulphoxide
MeOH=methanol
EtOH=ethanol
THF=tetrahydrofuran
EtOAc=ethyl acetate

EXAMPLE 1

4-[2-(2,2,2-Trifluoroethyl)guanidino]-2-methanesulphinylpyrimidine (140 mg.) was added to a stirred mixture at 50° of t-butanol (10 ml.), NaH (48 mg. of a 50% w/w dispersion in oil) and 1-(2-hydroxyethyl)imidazole, and the mixture stirred at 50° for 2 hours and then evaporated to dryness. The residue was partitioned between aqueous 1N HCl and ether and the aqueous phase basified with aqueous 10N NaOH and extracted with EtOAc. The EtOAc extract was dried and evaporated to dryness and the residue recrystallised from EtOAc to give 1-[2-(4-[2-(2,2,2-trifluoroethyl)-guanidino]pyrimid-2-yloxy)ethyl]imidazole (135 mg.), m.p. 149°-150°.

EXAMPLES 2-14

The process of Example 1 was repeated using the appropriate starting materials to give the following compounds:

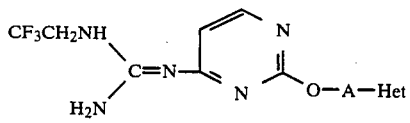

| Example | —A— | —Het | Salt | m.p. °C. | Yield % |
|---|---|---|---|---|---|
| 2 | —CH(CH₃)CH₂— | imidazol-1-yl | 2 maleate | 137–139 | 51 |
| 3 | —(CH₂)₃— | 2-methylimidazol-1-yl | 2 maleate | 261–263 | 34 |
| 4 | —(CH₂)₃— | 2-formylpyrrol-1-yl | maleate | 171–173 | 49 |
| 5 | —(CH₂)₃— | 2-oxopyridin-1-yl | maleate | 149–151 | 41 |
| 6 | —(CH₂)₃— | imidazol-1-yl | 2 maleate | 168 | 42 |
| 7 | —(CH₂)₃— | 1,2,4-triazol-1-yl | maleate | 271–273 | 43 |
| 8 | —(CH₂)₃— | 3-methyl-1,2,4-triazol-1-yl | maleate | — | 23 |

-continued

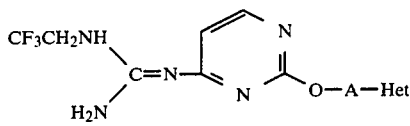

| Example | —A— | —Het | Salt | m.p. °C. | Yield % |
|---|---|---|---|---|---|
| 9 | —(CH₂)₃— | -N N—CH₃ (dioxopiperazinyl) | 1.25 maleate | 132–136 | 27 |
| 10 | —CH₂—C₆H₄— | -N (piperidinyl) | maleate | 177–180 | 19 |
| 11 | —(CH₂)₃— | -N-N=N / N—NH₂ (aminotriazole) | maleate | 186 (decomp) | 13 |
| 12 | —(CH₂)₃— | -N-N=N / NH₂ (aminotetrazole) | 1.25 maleate | 152 (decomp) | 47 |
| 13 | —(CH₂)₃— | -N-N / NH₂ (aminotriazole) | maleate | — | 8 |
| 14 | —(CH₂)₃ | -N-N / NH₂ | maleate | — | 23 |

Notes

In the above Table the pyrimid-2-yloxy group is attached to the left hand bond of group —A— and the heterocyclic group (—Het—) is attached to the right hand bond of group —A—. Thus, for example, the structure of the product in Example 2 is:

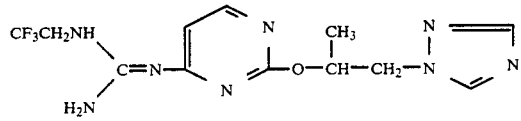

EXAMPLE 2

The starting material may be prepared as follows. A mixture of 1,2,4-triazole (5 g.) and 4-methyl-1,3-dioxolan-2-one was heated at 150° for 18 hours. Concentrated aqueous hydrochloric acid (8 ml.) was added dropwise to the ice-cooled mixture and the mixture was washed with chloroform. The aqueous phase was neutralised with aqueous potassium carbonate solution and extracted with chloroform, and the chloroform extract was dried and evaporated to dryness to give 1-(2-hydroxypropyl)-1,2,4-triazole (7.8 g.) which was characterised as the hydrogen oxalate, m.p. 110°–112° (after crystallisation from EtOH).

EXAMPLE 3

The starting material may be prepared as follows. A mixture of 2-methylimidazole (6.15 g.), a 50% w/w dispersion of sodium hydride in oil (5.4 g.) and DMF (20 ml.) was treated with 3-chloropropanol (10.6 g.) and the mixture heated at 100° for 24 hours and then evaporated to dryness. The residue was treated with concentrated aqueous hydrochloric acid (8 ml.) and the solution washed with chloroform, and then basified with potassium carbonate. The mixture was extracted with chloroform, and the extract was dried and evaporated to dryness to give 2-methyl-1-(3-hydroxypropyl)imidazole which was used without further purification.

EXAMPLE 4

The starting material may be prepared as follows. A solution of 2-formylpyrrole (1.0 g.) and a 50% w/w dispersion of sodium hydride in oil (0.72 g.) in DMF (20 ml.) was treated with 3-chloropropanol (1.03 g.) and the mixture heated at 90° for 18 hours and then evaporated to dryness. The residue was partitioned between water and ether, and the ether phase was dried and evaporated to dryness to give 1-(3-hydroxypropyl)-2-formylpyrrole (1.48 g.) which was used without further purification.

EXAMPLES 5-9

The starting materials may be prepared by the procedure described for the preparation of the starting material for Example 3, using the appropriate heterocycle in place of 2-methylimidazole.

EXAMPLE 8

The product is a 50:50 mixture of the 3-methyl-1,2,4-triazol-2-yl and 3-methyl-1,2,4-triazol-1-yl derivatives. The n.m.r. in $d_6$DMSO of this mixture was as follows: 2.3 (m, 5H); 4.3 (m, 6H); 6.6 (d, 1H); 7.7 (s, 0.5H); 8.2 (s, 0.5H); 8.2 (d, 1H).

EXAMPLE 10

The starting material may be prepared by the procedure described for the preparation of the starting material for Example 3 using 3-chloromethylphenol and piperidine.

EXAMPLES 11 AND 12

The starting materials may be prepared as follows:
5-Aminotetrazole (2.1 g.) and 3-chloropropanol (2.1 ml.) were added to aqueous sodium hydroxide (1 g. in 20 ml.) and the mixture heated at 90° for 18 hours. The resulting solution was evaporated and the residue extracted with hot EtOH. The EtOH extracts were evaporated and the residue extracted with EtOAc to give a colourless oil which was a mixture of isomers. These were separated on a column of silica gel using EtOAc/MeOH/aqueous ammonia (s.g. 0.880) 6:1:1 v/v/v as eluant to give 1-(3-hydroxypropyl)-5-aminotetrazole as a white solid (0.2 g.) and 2-(3-hydroxypropyl)-5-aminotetrazole as a gum (1.0 g.).

EXAMPLES 13 AND 14

The starting materials may be prepared as follows:
3-Amino-1,2,4-triazole (2.1 g.) was added to a solution of sodium hydroxide (1 g.) in water (15 ml.) and this solution treated with 3-chloropropanol (2.5 ml.). The mixture was heated on the steam bath for 18 hours and evaporated. The residue was extracted with hot EtOAc to give on evaporation a gum which was partly purified by medium pressure chromatography using chloroform/MeOH/aqueous ammonia (s.g. 0.880) 9:1:0.5 v/v/v as eluant to give 2-(3-hydroxypropyl)-3-aminotriazole [containing 25% of 1-(3-hydroxypropyl)-3-aminotriazole] and 1-(3-hydroxypropyl)-3-aminotriazole [containing 25% of 2-(3-hydroxypropyl)-3-aminotriazole]. These intermediates were used without further purification.

EXAMPLE 13

The product (60% of the indicated isomer) had the following n.m.r. in $d_6$DMSO:-2.0 (m, 2H); 4.2 (m, 6H); 6.6 (d, 1H); 7.4 (s, 1H); 8.4 (d, 1H).

EXAMPLE 14

The product (80% of the indicated isomer) had the following n.m.r. in $d_6$DMSO:-2.0 (m, 2H); 4.2 (m, 6H); 6.6 (d, 1H); 8.0 (s, 1H); 8.4 (d, 1H).

EXAMPLE 15

A mixture of 4-[2-(2,2,2-trifluoroethyl)guanidino]-2-(3-aminopropylthio)pyrimidine (0.31 g.), phenyl N-(2,2-dimethoxyethyl)carbamate (0.27 g.) and acetonitrile (5 ml.) was heated under reflux for 18 hours and then evaporated to dryness. The residue was partitioned between ether and N aqueous hydrochloric acid, and the aqueous phase was basified and extracted with EtOAc. The extract was dried and evaporated to dryness. The residue was dissolved in concentrated aqueous hydrochloric acid and the solution kept at room temperature for two hours and then evaporated to dryness. The residue was partitioned between water and ether. The aqueous phase was basified and extracted with EtOAc and the extract dried and evaporated to dryness. A solution of the residue in acetone was added to a solution of maleic acid in acetone, and the precipitate collected and recrystallised from aqueous EtOH to give 2-hydroxy-1-[3-(4-[2-(2,2,2-trifluoroethyl)-guanidino]pyrimid-2-ylthio)propyl]imidazole hydrogen maleate (0.16 g.), m.p. 152°–155°.

The starting material may be prepared as follows:
Phenyl chloroformate (1.73 g.) was added to a vigorously stirred solution of 2,2-dimethoxyethylamine (1.05 g.) and potassium carbonate (1.39 g.) in water (20 ml.), and the mixture stirred at room temperature for 2 hours. The mixture was extracted with ether, and the ether extract dried and evaporated to dryness to give phenyl N-(2,2-dimethoxyethyl)carbamate (1.5 g.) which was used without further purification.

EXAMPLE 16

A solution of ethyl 2-[3-(3-[4-(2-[2,2,2-trifluoroethyl]-quanidino)pyrimid-2-ylthio]propyl)ureido]acetate (0.08 g.) in MeOH (5 ml.) was treated with sodium methoxide (0.02 g.) and the solution kept at room temperature for two hours and then evaporated to dryness. The residue was dissolved in a small volume of water and the pH of the solution adjusted to 7 with dilute aqueous HCl and then extracted with EtOAc. The extract was dried and evaporated to dryness. A solution of the residue in acetone was added to a solution of maleic acid in acetone and the crystalline precipitate collected to give 2,4-dihydroxy-3-[3-(4-[2-(2,2,2-trifluoroethyl)guanidino]-pyrimid-2-ylthio)propyl]imidazole hydrogen maleate (0.05 g.), m.p. 195°–196°.

The starting material may be prepared as follows:
Phenyl chloroformate (1.8 g.) was added to a vigorously stirred solution of glycine ethyl ester hydrochloride (1.4 g.) and sodium hydrogen carbonate (1.85 g.) in water (20 ml.) and the mixture stirred at room temperature for 2 hours. The mixture was extracted with ether and the ether extract dried and evaporated to dryness to give ethyl 2-(phenoxycarbamoyl)acetate (2.2 g.).

A mixture of 4-[2-(2,2,2-trifluoroethyl)guanidino-2-(3-aminopropylthio)pyrimidine (0.31 g.), ethyl 2-(phenoxycarbamoyl)acetate (0.25 g.) and acetonitrile was heated under reflux for 18 hours and then cooled. The solid which crystallised was collected and recrystallised from acetonitrile to give ethyl 2-[3-(3-[4-(2-[2,2,2-trifluoroethyl]guanidino)pyrimid-2-ylthio]-propyl)ureido]acetate (0.14 g.), m.p. 165°–166°.

EXAMPLE 17

A mixture of 4-[2-(2,2,2-trifluoroethyl)guanidino]-2-(3-aminopropoxy)pyrimidine (0.23 g.), dimethyl methylsulphonylimido)dithiocarbonate (0.16 g.) and acetonitrile (5 ml.) was stirred at room temperature for 18 hours and then treated with N-methyl-2,2-diethoxyethylamine (0.15 g.). The mixture was heated under reflux for 18 hours, treated with a further 0.15 g. of N-methyl-2,2-diethoxyethylamine, and heated under reflux for a further 24 hours. The mixture was evaporated to dryness and the residue partitioned between N aqueous hydrochloric acid and ether. The aqueous phase was basified with 10N aqueous NaOH and extracted with EtOAc and the extract dried and evaporated to dryness.

A mixture of the residue and concentrated aqueous hydrochloric acid (2 ml.) was heated at 90° for 0.5 hours and then diluted with water. The solution was washed with ether, basified and extracted with EtOAc and the extract was dried and evaporated to dryness. A solution of the residue in acetone was added to a solution of maleic acid in acetone, and the precipitate was collected and recrystallised from EtOH to give 1-methyl-2-methylsulphonylimino-3-[3-(4-(2,2,2-trifluoroethyl)-guanidino]pyrimid-2-yloxy)propyl]-4-imidazoline hydrogen maleate (0.13 g.), m.p. 176°-177°.

EXAMPLE 18

To 4-[2-(2,2,2-trifluoroethyl)guanidino]-2-[5-(2-benzyloxycarbonylaminoacetylamino)pentyl]pyrimidine (0.2 g.) was added 13 ml. of a solution of potassium hydroxide (0.096 g.) in EtOH (50 ml.), and the mixture was heated under reflux for 35 minutes. The mixture was evaporated in vacuo, a few drops of aqueous HOAc was added to the residue, followed by sodium bicarbonate solution until pH 7 was obtained. The mixture was extracted with EtOAc, the extract dried and evaporated to give a pale yellow solid. This was dissolved in a small volume of hot EtOH and a solution of maleic acid (0.05 g.) in EtOH (0.5 ml.) added. There was obtained 2,4-dihydroxy-3-(5-[4-(2-[2,2,2-trifluoroethyl]guainidino)pyrimid-2-yl]pentyl)imidazole maleate (0.13 g.), m.p. 172°-174°.

The starting material may be prepared as follows:
The second, third, fourth, fifth and sixth parts of Example 4 in European Patent Publication No. 30092 were repeated using 5cyanopentylphthalimide in place of 4-cyanobutylphthalimide, to give 4-[2-(2,2,2-trifluoromethyl)guanidino]-2-(5-aminopentyl)pyrimidine.

To a solution of N-benzyloxycarbonylglycine (0.21 g.) in freshly distilled THF (5 ml.) was added N-methylmorpholine (0.1 g.). The resulting solution was stirred with cooling in an ice-salt bath, and a solution of i-butyl chloroformate (0.136 g.) in a small volume of THF was added in one portion. A precipitate formed immediately, and the mixture was stirred for cooling for 5 minutes. A solution of 4-[2-(2,2,2-trifluoroethyl)-guanidino]-2-(5-aminopentyl)pyrimidine (0.35 g.) in THF (10 ml.) was gradually added. The mixture was stirred at room temperature for 2 hours, then evaporated in vacuo. Sodium bicarbonate solution was added to the residue and the mixture extracted with EtOAc. The extract was dried (MgSO4) and evaporated to give a pale yellow oil which was purified by medium pressure chromatography, eluting with 5% v/v MeOH in methylene chloride to give 4-[2-(2,2,2-trifluoroethyl)-guanidino]-2-[5-(2-benzyloxycarbonylaminoacetylamino)pentyl]pyrimidine (0.17 g.) which was used without further purification.

EXAMPLE 19

Potassium cyanate (0.055 g.) was added in portions to a solution of 4-[2-(2,2,2-trifluoroethyl)guanidino]-2-[5-cyanomethylaminopentyl]pyrimidine (0.2 g.) in 80% v/v aqueous HOAc (2 ml.) at 0° and the mixture stirred for 1 hour, then heated at 60°-70° for 20 minutes. Concentrated aqueous hydrochloric acid (1 ml.) and water (0.6 ml.) were added and the mixture was heated on a steam bath for 30 minutes. On cooling, saturated sodium carbonate solution was added until the pH was approximately 7. The mixture was extracted with EtOAc, the extract dried (MgSO4) and evaporated. The residue was dissolved in EtOH (4 ml.) and a solution of maleic acid (0.065 g.) in EtOH (0.5 ml.) added. On standing there was obtained 2,4-dihydroxy-1-(5-[4-(2-[2,2,2-trifluoroethyl]guanidino)pyrimid-2yl]pentyl)imidazole maleate (0.2 g.), m.p. 183°-185°.

The starting material may be prepared as follows:
A mixture of 4-[2-(2,2,2-trifluoroethyl)guanidino]-2-(5-aminopentyl)pyrimidine (0.61 g.), chloroacetonitrile (0.17 g.) and triethylamine (0.23 g.) in EtOH (15 ml.) was heated under reflux for 7 hours. The solvent was evaporated and the residue was treated with sodium bicarbonate solution and extracted with EtOAc. The extract was dried (MgSO4) and evaporated to give an oil which was purified by medium pressure chromatography, eluting with 7.5% v/v MeOH in methylene chloride to give 4-[2-(2,2,2-trifluoroethyl)guanidino]-2-[5-cyanomethylaminopentyl]pyrimidine as a pale yellow solid which was used without further purification.

EXAMPLE 20

A tablet containing 200 mg. of 1-[3-(4-[2-(2,2,2-trifluoroethyl)guanidino]pyrimid-2-yloxy)propyl]imidazole may be prepared using ingredients in the following proportions:

|  | mg./tablet |
|---|---|
| (a) Tablet Core. | |
| Active agent | 200 |
| Lactose | 68.5 |
| Calcium carboxymethylcellulose | 22.5 |
| Polyvinylpyrrolidone | 6.0 |
| Magnesium stearate | 3.0 |
| (b) Tablet Coat | |
| Hydroxypropylmethylcellulose | 4.5 |
| Polyethylene glycol | 0.9 |
| Titanium dioxide | 1.35 |

The active agent, lactose and calcium carboxymethylcellulose are mixed. An aqueous solution of polyvinylpyrrolidone is added, and the mass is then mixed until it is suitable for granulation. The mass is then granulated and dried. The magnesium stearate is blended with the dried granules and the resulting mixture is compressed into tablets. The tablets are film-coated using an aqueous or solvent suspension of hydroxypropylmethylcellulose, polyethylene glycol and titanium dioxide.

We claim:
1. A guanidine derivative of the formula I:

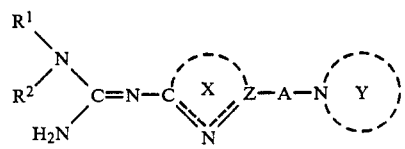

in which $R^1$ and $R^2$, which may be the same or different, are hydrogen or branched or unbranched 1-10C alkyl, 3-8C cycloalkyl or 4-14C cycloalkylalkyls, each alkyl, cycloalkyl or cycloalkylalkyl being optionally substituted by one or more halogens selected from fluorine, chlorine and bromine, provided that at least one of $R^1$ and $R^2$ is a halogen-substituted alkyl, cycloalkyl or cycloalkylalkyl, and provided that there is no halogen substituent on the carbon of the alkyl, cycloalkyl or cycloalkylalkyl which is directly attached to the nitrogen atom, or $R^2$ is hydrogen and $-R^1$ is of the formula II:

$$R^3-E-W- \qquad \text{II}$$

in which W is an unbranched 2-6C alkylene chain which is optionally substituted by one or two 1-4C alkyls, E is oxygen, sulphur, sulphinyl, sulphonyl or of the formula $NR^4$ in which $R^4$ is hydrogen or 1-6C alkyl, $R^3$ is hydrogen or an unbranched 1-6C alkyl which is optionally substituted by one or two 1-4C alkyls, or $R^3$ and $R^4$ are joined to form, together with the nitrogen to which they are attached, a pyrrolidine, piperidine, morpholine, piperazine or N-methylpiperazine ring, or $R^2$ is hydrogen and $R^1$ is hydrogen, 1-10C alkyl, 3-8C cycloalkyl, 4-14C cycloalkylalkyl, 3-6C alkenyl, 3-6C alkynyl, 1-6C alkanoyl, 6-10C aryl, 7-11C arylalkyl or 7-11C aroyl, the aryl, arylalkyl and aroyls being optionally substituted on the aryl ring by one or two substituents selected from fluorine, chlorine, bromine, 1-6C alkyl, 1-6C alkoxy, 1-6C alkylthio, trifluoromethyl, hydroxy and amino; in ring X the dotted line is a double bond on one side of the nitrogen and Z is carbon or nitrogen such that ring X is a 5-membered aromatic heterocyclic ring which contains at least one nitrogen and may optionally contain one or two additional hetero atoms selected from oxygen, nitrogen and sulphur, which heterocyclic ring may, where possible, carry one or two optional substituents, the optional substituents on ring X being selected from fluorine, chlorine, bromine, 1-6C alkyl, 1-6C alkoxy, 1-6C alkylthio, trifluoromethyl, hydroxy and amino; A is a 1-8C alkylene chain which is optionally substituted by one or two 1-3C alkyls and into which is optionally inserted, as part of the backbone of the chain, NH or 1-6C N-alkyl or one or two groups selected from oxygen, sulphur, cis and trans vinylene, ethynylene, phenylene and 5-7C alkylene, provided that no two insertions selected from oxygen, sulphur, NH and N-alkyl are directly attached one to the other, and provided that when an optional insertion is made in chain A which results in the inserted group being directly attached to ring Y the inserted group is other than oxygen, sulphur, NH or N-alkyl, or A is 5-7C cycloalkylene or phenylene; ring system Y is a heterocyclic ring system which is a 5- or 6-membered heterocyclic ring which may be saturated, partially unsaturated or fully unsaturated and which optionally contains one to three additional hetero atoms or groups selected from oxygen, nitrogen, sulphur, sulphinyl and sulphonyl and which optionally contains a fused benzene ring, ring system Y being optionally substituted on a nitrogen by a 1-6C alkyl and on a carbon of the heterocyclic ring, where possible, by one, two or three groups selected from halogen, 1-6C alkyl, 1-6C alkoxy, 1-6C alkanoyl, cyano, nitro, 2-6C alkoxycarbonyl, carbamoyl, 2-6C alkylcarbamoyl, 3-8C dialkylcarbamoyl, 1-6C alkanesulphonyl, hydroxy, amino, 1-6C alkylamino, 2-8C dialkylamino and methylsulphonylimino and the optional benzene ring being optionally substituted by one or two substituents selected from halogen, 1-6C alkyl, 1-6C alkoxy, 1-6C alkylthio, hydroxy and amino; and the pharmaceutically-acceptable acid-addition salts thereof.

2. A guanidine derivative of the formula I given in claim 1 in which $R^1$ and $R^2$ are selected from the group consisting of hydrogen, 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl, 2,2,3,3,4,4,4-heptafluorobutyl, 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl, 2-chloro-2,3,3,4,4-pentafluorocyclobutyl, (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl, (2-chloro-1,2,3,3,4,4-hexafluorocyclobutyl)methyl, methyl, ethyl, propyl, isopropyl, butyl, cyclopropyl, cyclobutyl, cyclopropylmethyl and cyclobutylmethyl provided that at least one of $R^1$ and $R^2$ is halogen-substituted, or $R^2$ is hydrogen and $-R^1$ is of the formula II given in claim 1 in which W is a 2-6C alkylene chain which is optionally substituted by one or two methyls E is oxygen, sulphur, sulphinyl or sulphonyl or of the formula $NR^4$ in which $R^4$ is hydrogen or methyl, $R^3$ is hydrogen or methyl, or $R^3$ and $R^4$ are joined to form, together with the nitrogen to which they are attached, a pyrrolidine, piperidine, morpholine, piperazine or N-methylpiperazine ring, or $R^2$ is hydrogen and $R^1$ is hydrogen, methyl, ethyl, propyl, isopropyl, butyl, cyclohexyl, cyclohexylmethyl, allyl, propargyl, acetyl, phenyl, benzyl or benzoyl, the phenyl, benzyl and benzoyls being optionally substituted on the phenyl ring by one or two substitutents selected from fluorine, chlorine, bromine, methyl, methoxy, methylthio, trifluoromethyl, hydroxy and amino; ring X is oxazole, thiazole, imidazole, 1,2,4-thiadiazole, 1,2,4-oxadiazole, 1,2,3-triazole, 1,2,4-triazole, pyrazole ring X being optionally substituted, where possible, by one or two substituents selected from fluorine, chlorine, bromine, methyl, methoxy, methylthio, trifluoromethyl, hydroxy and amino; —A— is phenylene, cyclopentylene, cyclohexylene, trimethylene, tetramethylene, pentamethylene, thioethylene, thiotrimethylene, thiotetramethylene, thiopentamethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, oxyethyleneoxymethylene, iminoethylene, iminopropylene, vinylenepropylene, oxymethylenevinylene, 1,3-phenylene, 1,3-cyclopentylene, methylene-1,4-phenylene, ethyleneoxymethylene-1,4-phenylene, oxy-1,3-phenylenemethylene or thiomethylene-ethynylenemethylene; ring system Y is of the formula IV, V, VI, VII, VIII, IX, X, XI or XII:

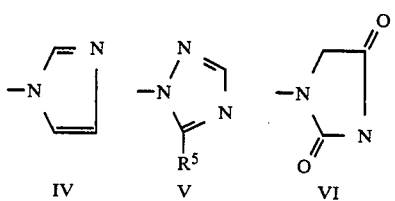

IV  V  VI

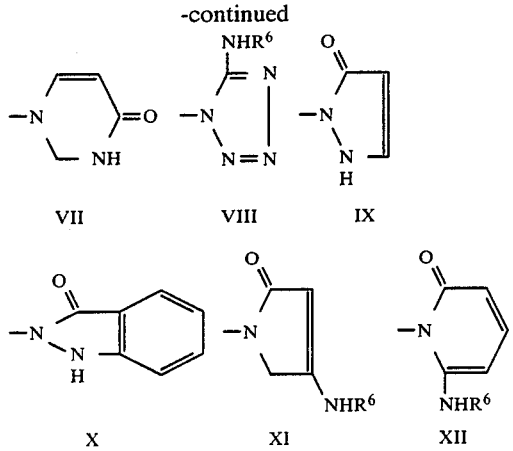

in which R⁵ is hydrogen or of the formula NHR⁶ and R⁶ is a hydrogen or methyl or ring system Y is 2-hydroxyimidazol-1-yl, 2,4-dihydroxyimidazol-3-yl, 2-methylimidazol-1-yl, 2-formylpyrrol-1-yl, 2-methylsulphonylimino-3-methyl-4-imidazolin-1-yl, 3-methyl-1,2,4-triazol-1-yl, 3-amino-1,2,4-triazol-1-yl, 5-amino-1,2,3,4-tetrazol-2-yl, 2-oxo-1,2-dihydropyrid-1-yl, 2,3-dioxo-4-methylpiperazin-1-yl or piperidin-1-yl: and the pharmaceutically-acceptable acid-addition salts thereof.

3. A guanidine derivative as claimed in claim 1 or 2 in which ring system Y is of the formula IV, V, VI, VII, VIII, IX, X, XI or XII given in claim 2 in which R⁵ is hydrogen or of the formula NHR⁶ in which R⁶ is hydrogen or methyl and ring X carries no optional substituent.

4. A guanidine derivative as claimed in claim 3 in which R² is hydrogen and R¹ is 2,2,2-trifluoroethyl.

5. A pharmaceutical composition which comprises a guanidine derivative as claimed in claim 1 in association with a pharmaceutically-acceptable diluent or carrier.

6. A method of inhibiting gastric acid secretion in a warm-blooded animal which comprises administering to the animal an effective amount of a compound of claim 1.

* * * * *